US008829212B2

(12) United States Patent
Maeda et al.

(10) Patent No.: US 8,829,212 B2
(45) Date of Patent: Sep. 9, 2014

(54) METHOD OF SEPARATING SOLID SALT FROM EPOXY RESIN SOLUTIONS

(75) Inventors: Shuji Maeda, Lake Jackson, TX (US); Ryosuke Tamai, Suginam-Ku (JP); Takashi Ikeda, Handa (JP); Joseph Weber, Himmelpforten (DE)

(73) Assignee: Dow Global Technologies LLC, Midland, MI (US)

( * ) Notice: Subject to any disclaimer, the term of this patent is extended or adjusted under 35 U.S.C. 154(b) by 538 days.

(21) Appl. No.: 13/127,508

(22) PCT Filed: Sep. 9, 2009

(86) PCT No.: PCT/US2009/056326
§ 371 (c)(1),
(2), (4) Date: May 4, 2011

(87) PCT Pub. No.: WO2010/071700
PCT Pub. Date: Jun. 24, 2010

(65) Prior Publication Data
US 2011/0263881 A1  Oct. 27, 2011

Related U.S. Application Data

(60) Provisional application No. 61/138,695, filed on Dec. 18, 2008.

(51) Int. Cl.
*C07D 301/32* (2006.01)
*C07D 301/27* (2006.01)
*C07D 303/04* (2006.01)
*C08G 59/00* (2006.01)

(52) U.S. Cl.
CPC .............. *C08G 59/00* (2013.01); *C07D 303/04* (2013.01); *C07D 301/23* (2013.01)
USPC .......................................... 549/541; 549/514

(58) Field of Classification Search
CPC ............................ C07D 301/32; C07D 303/04
USPC .................................................. 549/514, 541
See application file for complete search history.

(56) References Cited

U.S. PATENT DOCUMENTS

| | | | |
|---|---|---|---|
| 3,766,221 A | 10/1973 | Wilhelm Becker | |
| 3,957,831 A * | 5/1976 | Heilman | 549/515 |
| 4,499,255 A | 2/1985 | Wang et al. | |
| 4,751,280 A | 6/1988 | Pham et al. | |
| 4,877,857 A | 10/1989 | Shirtum et al. | |
| 6,420,464 B1 | 7/2002 | Kuboki et al. | |
| 2007/0299163 A1 | 12/2007 | Hwang et al. | |
| 2010/0331494 A1* | 12/2010 | Young et al. | 525/403 |
| 2011/0039982 A1* | 2/2011 | Hefner et al. | 523/400 |

FOREIGN PATENT DOCUMENTS

| | | |
|---|---|---|
| EP | 0356854 B1 | 9/1993 |
| EP | 0905178 A1 | 3/1999 |
| EP | 1070743 A2 | 1/2001 |
| WO | 2005015309 A2 | 2/2005 |
| WO | 2006085494 A1 | 8/2006 |
| WO | 2007146521 A1 | 12/2007 |

OTHER PUBLICATIONS

Database WPI Week 200302 Thomson Scientific, London, GB; AN2003-021913 XP002553909 & JP2002226535A (Showa High Polymer Co Ltd) Aug. 14, 2002), Abstract.
Database WPI Week 200245 Thomson Scientific, London, GB; AN2002-420228 XP002553910 & JP2002037851A (Sakamoto Yakuhin Kogyo KK) Feb. 6, 2002, Abstract.
Database WPI Week 199601 Thomson Scientific, London, GB; AN1996-006986 XP002556360 & JP07286030A (Dainippon Ink & Chem Inc) Oct. 31, 1995, Abstract.
Database WPI Week 199029 Thomson Scientific, London, GB; AN1990-221225 XP002556361 & JP02150412A (Mitsui Petrochem Ind Co Ltd) Jun. 8, 1990, Abstract.
PCT/US09/056326 , International Preliminary Report on Patentability.
PCT/US09/056326, Search Report and Written Opinion.

* cited by examiner

*Primary Examiner* — Mark Eashoo
*Assistant Examiner* — Megan McCulley

(57) ABSTRACT

Use a centrifuge, especially a peeler centrifuge, that has a coarse salt particle layer deposited on its screen to effect recovery of an epoxy resin, especially a liquid epoxy resin, from a product slurry, which epoxy resin has a lower residual salt content than an epoxy resin recovered without use of the coarse salt particle layer.

10 Claims, No Drawings

METHOD OF SEPARATING SOLID SALT FROM EPOXY RESIN SOLUTIONS

This application is a non-provisional application claiming priority from the U.S. Provisional Patent Application No. 61/138,695, filed on Dec. 18, 2008, entitled "METHOD OF SEPARATING SOLID SALT FROM EPDXY RESIN SOLUTIONS," the teachings of which are incorporated by reference herein, as if reproduced in full hereinbelow.

This invention relates to a method for separating solid salts from an epoxy resin solution, especially a solution containing a liquid epoxy resin (LER).

In manufacturing epoxy resins by reacting a polyhydric phenol, an epihalohydrin and an alkali metal hydroxide or an alkaline earth metal hydroxide, a crude reaction product typically contains a solid inorganic halide salt byproduct, an aqueous brine solution of the inorganic halide salt byproduct or a mixture of an aqueous brine and solid salt. If one reacts the polyhydric phenol, epihalohydrin and alkali metal or alkaline earth metal hydroxide in conjunction with water removal, solid alkali metal halide salts or alkaline earth metal halide salts precipitate out of solution and substantially no aqueous brine is present.

In some processes, separation of such solid salts from epoxy resins involves filtration or centrifugation, either of which yields a solid salt cake that contains liquid contaminants. Such contaminants include epoxy resin, epihalohydrin, any solvent(s) used to facilitate epoxy resin preparation, and reaction products other than the epoxy resin. The liquid contaminants, when present, limit potential reuse of the solid salt cake or pose some challenges in disposing the solid salt cake. A desire exists for modifications of such processes that lead to reduced liquid contaminant levels, preferably to very low liquid contaminant levels, especially those that approach, if not equal, zero enhance potential reuse of the solid salt cake or reduce challenges in solid salt cake disposal.

European Patent (EP) 0 356 854 B1 (Gammill et al.) discloses a method for removing relatively high boiling organic chemical contaminants from a contaminated material by washing the contaminated material with at least one solvent selected from ketones, and alcohols in which the organic chemical contaminant(s) is/are soluble at the treatment temperature. The contaminated material is an inorganic salt, such as the inorganic halide salt byproduct noted above, contaminated with reaction products of epihalohydrin and water, and with epihalohydrins, aromatic hydrocarbons and glycol ethers.

U.S. Pat. No. 4,751,280 to Pham et al. discusses preparation of epoxy resins. Pham et al. teaches, in part, removing insoluble materials from the reaction mixture by any suitable mechanical solid separation means, e.g. filtration, centrifugation and combinations thereof.

Soviet Union Patent (SU) 245368 to Rozentuler relates to a method of epoxy resin purification during resin production, especially during epoxy Novolak resin production, in which a reaction product comprises an epoxide resin—solvent liquid phase and a solid inorganic salt phase. Rozentuler teaches use of filtration to separate the solid inorganic salt phase from the epoxide resin—solvent liquid phase.

Czech Patent (CS) 190218 to Dobas et al. teaches separation of epoxy resins from reaction mixtures that comprise an epoxy resin—epichlorohydrin solution and solid salt by separation, either by gravitation or centrifugation, neither of which is linked to a particular apparatus, into a salt layer and a resinous layer that primarily comprises epichlorohydrin (I) and the epoxy resin.

In some aspects, this invention is an improved method for producing a LER, which method comprises a) reacting, with water removal, a polyhydric phenol, an epihalohydrin and an alkali metal hydroxide or alkaline earth metal hydroxide, to yield a product slurry that comprises LER, epihalohydrin, and a precipitated, solid alkali metal halide salt or a precipitated, solid alkaline earth metal halide salt, and b) separating the precipitated alkali metal halide salt or alkaline earth metal salt from the product slurry, wherein the improvement comprises a) effecting separation of the alkali metal salt or alkaline earth metal salt from the product slurry using a filtering-type basket centrifuge that has an internal slurry feed, a centrifuge basket, and an integral screen, the screen being used with or without at least one of an optional filter cloth or other porous barrier, which screen and optional filter cloth or other porous barrier retains solid material but allows liquid to pass through, said screen being disposed on an outer surface of the centrifuge basket and b) disposing a layer of coarse salt particles on an inner surface of the centrifuge, said coarse salt particles lying atop an inner surface of the screen, or when at least one of the optional filter cloth or other porous barrier is used in conjunction with the screen, atop an inner surface of said optional filter cloth and/or other porous barrier, the coarse salt particles having an average particle size that exceeds that of the precipitated alkali metal salt or alkaline earth metal salt particles contained in the product slurry, whereby the precipitated alkali metal salt or precipitated alkaline earth metal salt forms a layer on a slurry feed side of the layer of coarse salt particles. The filtering-type centrifuge is sometimes referred to as a peeler.

In some aspects of the improved process, separating the precipitated alkali metal halide salt or alkaline earth metal halide salt from the product slurry occurs as a batch process that comprises at least one sequential series of substeps, said substeps being a) filling a receiving portion of a centrifuge with an amount of the product slurry, the amount being less than that which overfills the receiving portion of the centrifuge, b) allowing a portion of liquids contained in the reaction mixture to drain through the layer of coarse salt particles, and c) operating the centrifuge at a speed sufficient to substantially effect separation of the amount of the reaction product mixture into a resin mixture component that substantially passes through the layer of coarse salt particles and the layer of precipitated alkali metal halide salt or alkaline earth metal halide salt.

The precipitated, solid alkali metal halide salt or precipitated, solid alkaline earth metal salt may be referred to as a "solid inorganic halide salt" or, alternatively, as a "byproduct" or "inorganic salt byproduct". With at least a portion of the inorganic salt byproduct being deposited on the layer of coarse salt particles, any epoxy resin from the product slurry that passes through the layer of coarse salt particles has a lower salt content than epoxy resin separated from the same product slurry using the same centrifuge, but without the layer of coarse salt particles.

"Epoxy resin" refers to a reaction product of a polyhydric phenol and an epihalohydrin. The epihalohydrin and the polyhydric phenol are present in amounts sufficient to provide a mole-equivalent ratio of moles of epihalohydrin to moles of phenolic hydroxide moieties of the polyhydric phenol that equals or exceeds (>) 1:1. An epoxy resin that is liquid at room temperature (nominally 25 degrees centigrade (° C.) is commonly referred to as a LER.

U.S. Pat. No. 4,499,255 to Wang et al. teaches preparation of LERs by reacting at least one compound having at least one aromatic hydroxyl group or aromatic amine group per molecule with an excess of at least one epihalohydrin in the presence of an alkali metal hydroxide.

In some aspects, this invention is a method for preparing a filtering-type basket centrifuge, especially a peeler centrifuge, for use in the improved method for producing an epoxy resin. The method for preparing the centrifuge comprises establishing a layer of coarse salt particles, which layer has a slurry feed side and a filtrate side and disposing said layer such that the slurry feed side of the layer first contacts product slurry from a source of said product slurry and the filtrate side is spaced apart from said product slurry source. The method preferably comprises substeps a) introducing an aliquot of the coarse salt particles into the centrifuge, and b) forming the aliquot into a layer, more preferably a layer with a substantially uniform thickness. The method applies to LERs as well as to other epoxy resins that are semi-solid or solid at room temperature, but dissolved in an organic solvent (e.g. excess epichlorohydrin) or solvent mixture.

When ranges are stated herein, as in a range of from 2 to 10, both end points of the range (e.g. 2 and 10) and each numerical value between the end points, irrespective of whether such value is a rational number or an irrational number is included within the range unless otherwise specifically excluded.

Preparation of the product slurry that comprises epoxy resin, an inorganic salt byproduct and epihalohydrin occurs via known technology; such as that disclosed in U.S. Pat. No. 4,751,280.

The polyhydric phenol, also known as an "aromatic hydroxyl-containing compound", preferably contains at least one aromatic hydroxyl group and includes phenols, bisphenols, novolac resins, polyvinyl phenols and corresponding amine compounds as taught by Wang et al. (U.S. Pat. No. 4,499,255) at column 1 line 65 through column 4, line 59. See also, Shirtum et al. (U.S. Pat. No. 4,877,857) at column 5, line 8 through column 7, line 65. Other preferred phenolic compounds include those taught by Berman et al. (U.S. Pat. No. 4,727,119) at column 4, lines 12-43.

Suitable epihalohydrins include those taught by Shirtum et al. (U.S. Pat. No. 4,877,857) at column 7, line 65 through column 8, line 14.

The hydroxide may be an alkali metal hydroxide (e.g. sodium hydroxide or potassium hydroxide) or an alkaline earth hydroxide (e.g. calcium hydroxide). The hydroxide is preferably an alkali metal hydroxide, more preferably sodium hydroxide.

The filtering-type basket centrifuge, preferably a peeler centrifuge, yields a solid cake of inorganic salt byproduct with a lower residual liquid content than that attainable with a solid bowl centrifuge. The peeler centrifuge comprises a rotating centrifuge basket and a scraper or "peeler" mechanism for removing the deposited solid cake from the basket. The centrifuge basket has a screen that is optionally, but preferably used in conjunction with a filter cloth or other porous barrier. The screen and optional, but preferable, combination with a filter cloth or other porous barrier, simply needs to be strong enough to retain solid material, but allow a liquid to pass through, is disposed on the centrifuge basket's outer surface. The screen may be fabricated from any material, including metal or plastic, as long as it is strong enough to retain solid material, yet porous enough to allow a liquid to pass through. At least one of the filter cloth or other porous barrier material, when used, lies atop the screen proximate to the coarse salt particle layer and remote from the centrifuge basket's outer surface. The scraper mechanism has a height or thickness adjustment that allows it to remove a substantial portion of the solid cake of inorganic salt byproduct, yet leave a layer of uniform depth, also known as a "heel cake", on the filter cloth, screen or other porous barrier. By retaining a heel cake, one avoids direct contact between the scraper mechanism and the filter cloth, screen or other porous barrier. The rotating centrifuge basket may be disposed such that its axis of rotation is either horizontal or vertical with respect to a surface upon which the peeler centrifuge sits. Based upon its disposition, one may refer to the basket centrifuge as a vertical basket centrifuge or a horizontal basket centrifuge and the peeler centrifuge as, for example, a horizontal peeler centrifuge, or a vertical peeler centrifuge. In one optional arrangement, the perforated centrifuge basket has an outer cylindrical shell to capture filtrate. The bowl is preferably connected to a chamber that provides a siphoning action to increase pressure differential across the filter cloth, screen or other porous barrier and the cake. Centrifuges which utilize this siphoning action may be referred to as, for example, rotary siphon peeler centrifuges. Peeler centrifuges manufactured by Krauss Maffei Process Technology, GMBH provide particularly preferred results.

For at least some aspects of this invention, prepare the centrifuge, preferably a peeler centrifuge, for use in separating inorganic salt byproduct particles from the product slurry by first depositing a layer of coarse salt particles on the centrifuge screen, filter cloth or other porous barrier material. Inorganic salt byproduct particles, i.e. those formed during the reaction between epihalohydrin and a polyhydric phenol, typically have a particle diameter of less than 200 µm and often less than 100 µm. When one effects deposition of a salt cake comprising, consisting essentially of or even consisting of such inorganic salt byproduct particles directly on the screen of a centrifuge, that salt cake of inorganic salt byproduct particles provides greater resistance to fluid flow than a salt cake comprising the coarse salt particles described herein. A greater resistance to fluid flow translates to a longer time for a given volume of fluid to permeate through the salt cake and, consequently, a lower centrifuge capacity per unit time.

During centrifuge operation to separate inorganic salt byproduct from the product slurry, a layer of inorganic salt byproduct particles deposits on an inner or slurry side (disposed remote from the centrifuge screen, filter cloth or other porous barrier material) of the layer of coarse salt particles. The layer of inorganic salt byproduct particles, in combination with the layer of coarse salt particles, provides less fluid flow resistance than a layer of similar thickness deposited directly on the screen and composed solely of the inorganic salt byproduct particles.

A preferred technique for depositing the layer of coarse salt particles on the centrifuge screen, filter cloth or other porous barrier material, or combination of screen and filter cloth or other porous barrier material, involves introducing a slurry of the coarse salt particles in a liquid (e.g. an organic solvent) that does not function as a solvent for the coarse salt particles into the centrifuge. If desired, a saturated brine may be used in place of the organic solvent. Operation of the centrifuge removes solvent or brine from the slurry and distributes or spreads the coarse salt particles over the centrifuge screen, filter cloth or other porous barrier material, or combination of screen and filter cloth or other porous barrier material. An alternate technique uses a screw conveyor or other mechanical means to introduce coarse salt particles, rather than a slurry of coarse salt particles, into the centrifuge. Operation of the centrifuge during or after addition of the coarse salt particles effects distribution of the coarse salt particles. The liquid, preferably an organic solvent, is more preferably an organic solvent already used in epoxy resin production processes as a wash liquid in order to simplify treatment of organic liquids. Use the centrifuge's scraper or "peeler" mechanism to mechanically and evenly distribute the salt particles across the filter cloth or screen or combination thereof, preferably to a uniform layer of desired depth or thickness.

The coarse salt particles that form the layer on the centrifuge screen, filter cloth or other porous barrier material have a size within a size range that is preferably from greater than 100 micrometers ($\mu$m) to 2000 $\mu$m. The coarse salt average particle size range is more preferably from 200 $\mu$m to 1000 $\mu$m and still more preferably from 300 $\mu$m to 600 $\mu$m. If the coarse particles are too fine, e.g. less than 100 $\mu$m such that they approach or equal the inorganic halide salt byproduct particles contained in they product slurry, then resistance to fluid flow inherent in such a layer of coarse salt particles approximates that of a layer composed solely of inorganic halide salt byproduct particles with an average particle size of 100 $\mu$m and resulting filtration rates become uneconomically slow. If the coarse particles are too large, e.g. over 2000 $\mu$m, they lose their effectiveness in removing the inorganic halide salt byproduct particles. In other words, many of the byproduct particles pass through a bed of the coarse salt particles so the epoxy resin is not as pure as desired, especially for commercial purposes.

The heel cake layer preferably has a thickness sufficient to be effective at reducing permeation resistance of deposited salt cake (inorganic salt byproduct particles), but not so thick as to substantially reduce usable depth of the centrifuge basket. Mechanical limitations inherent in some current centrifuge designs typically provide a minimum heel cake layer thickness of 10 millimeters (mm), with a preferred thickness, given those limitations, lying within a range of from 10 millimeters (mm) to 150 mm. The range is more preferably from 10 mm to 100 mm, still more preferably from 20 mm to 60 mm and even more preferably from 30 mm to 40 mm. Other current centrifuge designs allow one to further reduce heel cake thickness, with beneficial results at a thickness as low as 1 mm or even lower. If the layer is too thin, e.g. less than 0.1 mm, it fails to prevent clogging of a filter cloth upon which the heel cake rests. It also fails to provide adequate filtration capacity to trap enough of the solid byproduct particles to yield a recovered epoxy resin of sufficient purity to meet commercial specifications for many applications. If the layer is too thick, e.g. more than 100 mm, especially more than 150 mm, it takes up so much of the centrifuge's capacity or volume that the centrifuge can only process uneconomically small aliquots of product slurry per unit of time.

In order to minimize cross-contamination potential, the precipitated byproduct salt particles and the coarse salt particles preferably have a similar, more preferably identical, composition in terms of inorganic halide, with sodium chloride being a preferred inorganic halide. In other words, the particles of the coarse salt layer have a gross chemical composition substantially identical to that of salt particles contained in the product slurry. Commercially available coarse salt particles typically have a high purity, e.g. greater than (>) 95 wt % and preferably >98 wt %, based upon total salt particle weight, with a primary, if not sole, contaminant being water that is present from at least one of incomplete drying and reabsorption from air.

The product slurry may also contain an insoluble byproducts such as an insoluble copolymer of glycidol and epichlorohydrin. When present, these insoluble byproducts tend to deposit on the layer of coarse salt particles concurrent with deposition of the inorganic salt byproduct particles.

Over time, the layer of inorganic salt byproduct particles and, in at least some instances, a relatively thin, outer or slurry side thickness of the coarse salt particle layer tends to become plugged by such insoluble byproducts and, possibly, other solid materials, especially those that have an average particle size less than that of the inorganic salt byproduct particles. This effectively results in a reduction in filtration rate from that available when first introducing a product slurry to a fresh layer of coarse salt particles to a much slower rate.

Removing at least a portion of the inorganic salt byproduct layer, preferably all of the inorganic salt byproduct salt layer and at least a surface portion of the relatively thin slurry side thickness of coarse salt particle layer, preferably a thin layer and more preferably a thin, uniform layer or thickness from the slurry side of the coarse salt particle layer at least partially restores or improves filtration rates for a period of time. The period of time begins with removal of the thin layer and ends when filtration rates become slow enough that removal the inorganic salt layer and of another thin layer becomes desirable, if not necessary.

The relatively thin layer is preferably thick enough that its removal improves filtration rates, but not so thick as to cause one to prematurely replace or restore the coarse salt particle layer. The relatively thin layer has a thickness that preferably lies within a range of from 0.1 mm to 5 mm, more preferably from 0.2 mm to 1 mm. The thin layer may be much greater in thickness, e.g. >5 mm, but removal of that much of the heel cake does not appreciably enhance filtration rates over removal of less than (<) 5 mm. At the same time, removal of that much heel cake in a single step reduces heel cake life by, at least in this instance where one compares 0.5 mm and 6 mm, more than a factor of 10.

One may continue to remove thin layers of the coarse salt particle layer until one reaches a minimum heel cake layer thickness. Once filtration rates with that thickness become undesirably low, removing the heel cake and material deposited thereon in favor of establishing a new heel cake within parameters described above rises as a preferred course of action.

One may initiate removal of deposited inorganic byproduct salt particles and a thin layer of the coarse salt particles (sometimes referred to as a "partial scraping") either periodically or in response to a triggering event such as decrease in centrifuge capacity below a desired level. If one chooses to effect partial scraping on a periodic basis, anything within a range of from one partial scraping per hour to one partial scraping per ten days (240 hours) produces acceptable results. The range is preferably from one partial scraping every twelve hours to one partial scraping every five days.

As an alternative to removing and replacing the heel cake once it reaches a minimum practical thickness such as 10 mm, one can rebuild the heel cake layer thickness one or more times by halting the product slurry feed, introducing a coarse salt particle slurry feed to the centrifuge, operating the centrifuge with the coarse salt particle slurry feed until the heel cake thickness reaches a desired level, and then stopping the coarse salt particle slurry feed and restarting the product slurry feed. The coarse salt particle slurry feed preferably comprises a plurality of coarse salt particles and a non-solvating solvent such as epichlorohydrin.

Centrifuge manufacturers specify operating speed ranges, in terms of rpm, as well as maximum operating speed. Skilled artisans recognize that as between two different sizes of centrifuges, a smaller centrifuge has a higher maximum operating or rotation speed than a larger centrifuge. Skilled artisans also recognize that higher rotation speeds translate to higher gravitational or "G" forces which provide, in turn, faster settling speeds and higher filtration rates. While one may operate the centrifuge at any speed within a range specified by a manufacturer, operation at or near the maximum operating speed approaches, if not reaches, maximum filtration rates with consequent economic advantages over slower operating speeds.

Skilled artisans further recognize that a slurry processing rate also depends, at least in part, on product slurry solid content and slurry liquid viscosity. As between two different solid contents, a lower solid content will have a higher slurry processing rate than a higher solid content.

For a given product slurry precipitated solid salt byproduct content and as between two different filtration rates, a higher filtration rate translates to a higher centrifuge productivity level than a lower filtration rate. Accordingly, maximizing filtration rate becomes economically advantageous.

The product slurry typically comprises epoxy resin, unreacted epihalohydrin, and a solid particulate inorganic salt. The product slurry may also comprise other volatile materials such as an organic solvent. The layer of precipitated inorganic salt byproduct, and preferably any aliquot thereof, has a residual moisture or volatile content that is preferably no more than 25 wt %, more preferably no more than 20 wt % and still more preferably no more than 15 wt %. A residual moisture or volatile content of 0 wt % is not attainable from a practical perspective because of an adsorption isotherm.

With respect to filtrate, or material that passes through the layer of coarse salt particles, results become increasingly favorable as precipitated salt content of the filtrate decreases. Skilled artisans recognize that any precipitated salt content that passes through to the filtrate must be removed by another procedure, e.g. by washing. Accordingly, one seeks to maximize removal of the precipitated solid inorganic salt particles and the improved process disclosed herein provides more effective removal than use of the same equipment and the same slurry, but without the layer of coarse salt particles.

During centrifuge operation, especially of a peeler centrifuge, one preferably fills the centrifuge's receiving bowl or basket as full as possible with product slurry without overflowing the bowl or basket as an overflow equates to a spill and consequent loss of product. For a peeler centrifuge, product slurry enters a spinning centrifuge basket from inside the centrifuge. A 0 percent (%) fill level occurs when product slurry is at a level even with the centrifuge screen's inside surface. A 100% fill level occurs when product slurry is at a level even with the basket's inner annulus. Adding enough product slurry to exceed the 100% fill level causes spillage or overflow into the centrifuge's case. The fill level is preferably from 50% to 100%, more preferably from 60% to 100%, still more preferably from 70% to 100% and even more preferably from 90% to 100%.

Preferred practice of the improved method involves continuing to feed product slurry after reaching a desired fill level to at least maintain that fill level. One preferably stops feed of the product slurry only when a cake of salt byproduct particles reaches a desired maximum thickness. Any maximum thickness may be chosen as long as it is less than a thickness that effectively reduces centrifuge slurry processing capacity to a very low level, e.g. less than 5% of original capacity. The maximum thickness is typically a matter of operator optimization. In that case, stop the product slurry feed, allow liquid to filter through the layer of coarse salt particles, a step that typically lasts for two to three minutes, but may take more or less time depending upon permeability of combined of coarse salt particle layer and newly deposited inorganic salt byproduct particles as well as centrifuge operating speed. After this step, introduce a flow of wash liquid in an amount that is a fraction of total volume of product slurry feed to the centrifuge before initiating the flow of wash liquid. The fraction lies within a range of from 0.01 to 0.6, preferably from 0.05 to 0.3, each fraction being based upon total volume of product slurry feed. After introducing a desired fraction of wash fluid, stop the flow of wash liquid, allow the wash liquid to filter through the layer of coarse salt particles, and remove the heel cake.

A preferred practice involves feeding the product slurry to an operating (spinning) centrifuge as rapidly as possible consistent with avoiding overflow of the centrifuge bowl or basket. A minimum initial product slurry feed rate occurs when one observes onset of pronounced vibrations in the bowl. As one increases slurry feed rate above this level, the vibrations disappear. Initial product slurry feed rates, expressed in terms of kilograms per square meter of centrifuge bowl or basket area per hour ($kg/m^2/hr$), preferably range from 3000 $kg/m^2/hr$ to 10,000 $kg/m^2/hr$, more preferably from 4,000 $kg/m^2/hr$ to 8,000 $kg/m^2/hr$ and still more preferably from 4,000 $kg/m^2/hr$ to 6,000 $kg/m^2/hr$. Skilled artisans recognize that these product slurry feed rates may vary depending upon a variety of factors such as centrifuge maximum operating rate, precipitated solid inorganic salt particle size, coarse salt layer particle size and product liquid phase viscosity. Skilled artisans can readily adapt to such factors without undue experimentation.

An optional, but preferred, practice includes use of instrumentation to improve the operation of the centrifuge. For example, deploy one or more liquid level detectors within the centrifuge to detect liquid levels within a centrifuge basket during the operation of the centrifuge. The use of level detectors allows one to feed the slurry to the centrifuge at a maximum rate without overflowing the centrifuge basket.

Another preferred practice, especially suitable for batch centrifuge operations, specifies that one halt deliquoring operations before one completely deliquors the coarse salt layer or salt cake between feeds of slurry aliquots. In other words, salt cake remains fully saturated such that one substantially avoids creating air gaps across portions of either the coarse salt layer or a layer of newly deposited inorganic salt byproduct particles.

One may either discharge the inorganic salt byproduct layer from the centrifuge for further processing or subject the layer to further processing while it remains in the centrifuge. An object of further processing is a reduction in amount of epoxy resin retained on the salt cake. If one chooses to discharge the inorganic salt byproduct layer, a preferred practice involves stopping product slurry feed to the centrifuge and operating the centrifuge until permeation of liquid components of the product slurry appears to halt in order to minimize the inorganic salt byproduct layer's residual liquid content. Alternatively, if one chooses further processing in the centrifuge, purification of the inorganic salt byproduct layer comprises washing the inorganic salt byproduct layer with a solvent or solvent combination to reduce the layer's residual epoxy resin content from the content prior to washing.

Epichlorohydrin functions as a preferred solvent or a preferred component of a solvent combination. Other suitable solvents, which may be used instead of, or in combination with, epichlorohydrin include ketones and organic chemical solvents such as aromatic solvents and chlorinated organic solvents. Solvent selections preferably meet two criteria. First, they may, and preferably do, dissolve epoxy resin but have little, preferably no, tendency to dissolve the inorganic salt byproduct particles. Second, they should be easily recoverable from the inorganic salt byproduct particles or brine formed from such particles. In a most preferred practice, one uses the same solvent or solvent combination in both the reaction that leads to the product slurry and in washing the inorganic salt byproduct layer. See EP 0 356 854 noted and partially described above for a further description of preferred methods of washing inorganic salt cakes as well as other suitable solvents.

EXAMPLE 1

Use a pilot scale peeler centrifuge (HZ4OSI, Krauss Maffei) equipped with a horizontal basket with a 40 micrometer (μm) stainless steel screen and a filtration area of 2.69 square feet (ft$^2$) (2.5×10$^{-1}$ square meters (m$^2$)) to separate a slurry mixture that contains epichlorohydrin, 1-methoxy-2-propanol, LER, solid sodium chloride salt and glycidol-epichlorohydrin copolymer byproduct from an epoxy resin production reactor. The LER has an epoxy equivalent weight of 184 grams per equivalent (g/equiv). The slurry has a solid salt content of 23 wt %, based on total slurry weight.

Operate the centrifuge at a rotation speed and a filtration rate as shown in Table 1 below to yield a salt cake with a moisture content also shown in Table 1. Analysis of filtrate exiting the centrifuge shows that it has a free chloride ion content of 6 parts by weight per million parts by weight (ppm), based on total filtrate weight, as analyzed by titration with silver nitrate. Determine salt cake moisture content by placing a sample of the salt cake in an oven for three hours at a temperature of 130° C. and measuring weight loss by subtracting sample weight after treatment in the oven from sample weight before treatment in the oven and converting the difference to wt %. Table 1 also shows salt cake moisture content as wt % liquid or volatiles and filtrate salt (chloride ion) content for four iterations of the separation under conditions also shown in Table 1.

TABLE 1

| Run Number/ Parameter | Rotation Speed (rpm) | Feed Solid Salt Content (wt %) | Filtration Rate (lb/min/ft$^2$)/ (kg/min/m$^2$) | Cake Moisture Content (wt % liquid) | Filtrate Salt Content (ppm Cl$^-$) |
| --- | --- | --- | --- | --- | --- |
| 1 | 1000 | 23 | 3.6/18 | 9.0 | 6 |
| 2 | 1500 | 21 | 6.1/30 | 3.0 | 6 |
| 3 | 2120 | 4.5 | 21.9/107 | 3.5 | 7 |
| 4 | 2120 | 16 | 8.4/41 | 7.6 | Not measured |

The data presented in Table 1 demonstrate that one can attain residual salt contents of less than 10 ppm ionic chloride and solid cake moisture contents of less than 10 wt % liquid, based on total salt cake weight, without use of a coarse salt particle layer. In other words, a peeler centrifuge provides good separation of solid salt particles from organic liquids, both of which are part of the slurry mixture.

COMPARATIVE EXAMPLE A

Use a solid bowl centrifuge operating at a bowl speed of 2600 revolutions per minute (rpm) to effect separation of a LER slurry similar to that of Example 1. The slurry comprises epichlorohydrin, liquid epoxy resin and solid salt, with a solid salt content of 13% of the slurry by weight and a LER content of 31% of the slurry by weight. Collect samples of the solid salt cake from the centrifuge at two different times during centrifuge operation and analyze the salt cake for moisture content (wt % volatiles) as in Example 1 and for salt cake resin content (wt % resin, based on total salt cake weight).

Determine salt cake resin content by mixing a salt cake sample with methyl ethyl ketone (MEK), separating the salt from the MEK by filtration, drying the salt, measuring salt weight, evaporating the volatiles (MEK and epichlorohydrin) from the filtrate to recover the LER, weighing the LER and converting the LER weight to a wt % based upon salt cake sample weight prior to mixing with the MEK.

The first sample has a moisture content of 33.2 wt % and a salt cake resin content of 5.9 wt %. The second sample, taken later in time than the first sample, has a moisture content of 23.0 wt % and a salt cake resin content of 7.3 wt %.

Comparative Example A demonstrates that a solid bowl centrifuge is much less efficient than a peeler centrifuge (Example 1) for slurry mixture separation in terms of residual or cake moisture content (23 wt % for Comparative Example A versus no more than 9.0 wt % for Example 1).

EXAMPLE 2

Prepare a larger scale peeler centrifuge (Krauss-Mafei, Model HZ-160L, 160 cm inside diameter) for separation of a LER slurry mixture by distributing a layer of coarse solid salt particles (0.4 millimeter (mm) average particle size) over a combination of a filter cloth and a stainless steel screen, the filter cloth being disposed on the stainless steel screen. Effect distribution by using a screw conveyer to feed the solid salt particles via a nozzle into the centrifuge while its basket rotates at a speed of 950 rpm. Move the screw conveyor nozzle end to achieve a visually uniform and even distribution of the salt particles on the screen. Use the centrifuge scraper to mechanically and evenly distribute the salt particles across the screen to a uniform layer depth or thickness of 30 mm.

The epoxy resin slurry mixture has a LER content of 34 wt % and a solid salt content of 13 wt %, each wt % being based on total slurry mixture weight, with the balance of the mixture comprising epichlorohydrin and 1-methoxy-2-propanol.

Operate the centrifuge at a rotation speed of 950 rpm. Add the slurry mixture to the rotating or operating centrifuge basket at a feed rate sufficient to substantially fill the basket, then reduce the feed rate to a rate sufficient to maintain the basket at a nearly full, but not overflowing level. Continue reducing the feed rate in recognition of reduced salt layer permeability over time due at least in part to deposition of salt onto the coarse salt layer. Stop the slurry feed mixture after reaching a total slurry mixture feed amount of 2000 kilograms (kg). Continue operating the centrifuge at the 950 rpm rotation speed for 2.6 minutes (min) to allow reduction of liquid level within the centrifuge basket without fully deliquoring the coarse salt layer.

Wash the coarse salt layer in two stages with the centrifuge rotating at 950 rpm. In stage one, feed wash liquor from a second wash of a previous centrifuge batch to the basket and allow the wash liquor to permeate through the salt layer. In stage two, feed a liquid mixture of epichlorohydrin and 1-methoxy-2-propanol to the basket and allow the mixture to permeate through the salt layer. Recover the stage two wash liquid mixture and store it for use in a subsequent centrifuge batch as a stage one wash liquor. In each of stages one and two, the wash liquid mixture or wash liquor is present in a weight ratio of wash liquid to total slurry feed of 0.2.

After wash stage two, allow the centrifuge to spin at 950 rpm to deliquor the coarse salt layer. Use the centrifuge scraper to mechanically remove salt deposited from the slurry mixture down to the 150 mm depth of the coarse salt layer.

Remove a sample of the post-stage two mechanically removed salt and determine salt cake moisture content and salt cake resin content as in Comparative Example A. Table 2 below provides data for five iterations of the separation.

TABLE 2

| Run Number/ Parameter | Cake Moisture Content (wt % liquid) | Cake Resin Content (wt % resin) |
|---|---|---|
| 1 | 12.8 | 0.26 |
| 2 | 13.5 | 0.13 |
| 3 | 13.9 | 0.11 |
| 4 | 17.5 | 0.25 |
| 5 | 13.9 | 0.07 |

The data in Table 2 demonstrate that practice of the improved method of producing an epoxy resin wherein the centrifuge contains a layer of coarse salt particles, yields an improvement in both inorganic salt byproduct layer resin content and inorganic salt byproduct layer moisture content relative to use of a solid bowl centrifuge (Comparative Example A).

EXAMPLE 3

Using the centrifuge prepared in Example 2, replicate batch processing of the epoxy resin slurry mixture as described in Example 2 several times until the centrifuge begins to lose effectiveness in separation of the slurry as indicated by a decreased permeation rate of the liquid through the salt cake in the centrifuge to less than 5.2 pounds of slurry mixture per minute per square foot (lb/min/ft$^2$) (25 kilograms per minute per square meter (kg/min/m$^2$). Change the scraper's depth setting so it removes a thin (~0.5 mm) upper layer of the coarse salt particle layer in addition to removing the salt layer deposited during separation. With this removal, the coarse salt layer has a thickness of 29.5 mm rather than 30 mm. Resume separations, observing an increased effectiveness in slurry separation for a time with the lower coarse salt layer thickness. Once effectiveness decreases, replicate removal of a thin upper layer of the coarse salt particle layer down another 0.5 mm to a thickness of 29 mm. Continue successive iterations of multiple slurry separations and a thin layer removal until the coarse salt layer has a thickness of 10 mm, then remove remaining coarse salt layer particles and re-establish a new coarse salt layer of 30 mm thickness as in Example 2 before resuming slurry separation.

Example 3 suggests that an upper portion of the coarse salt particle layer becomes plugged or blocked off, possibly by accumulation of one or more of insoluble polymer and separated salt particles. Removal of that upper portion, irrespective of what causes plugging, reestablishes at least a portion of coarse salt particle layer slurry separation effectiveness. While this example uses a coarse salt layer thickness of 30 mm, one can use a different thickness as long as it is not so thick that it reduces centrifuge basket capacity for the slurry mixture to an uneconomically low level or so thin that it does not effect separation of the slurry.

What is claimed is:

1. An improved method for producing a liquid epoxy resin, which method comprises a) reacting, with water removal, a polyhydric phenol, an epihalohydrin and an alkali metal hydroxide or alkaline earth metal hydroxide, to yield a product slurry that comprises liquid epoxy resin, epihalohydrin, and a precipitated, solid alkali metal halide salt or a precipitated, solid alkaline earth metal halide salt, and b) separating the precipitated alkali metal halide salt or alkaline earth metal salt from the product slurry, wherein the improvement comprises effecting separation of the alkali metal salt or alkaline earth metal salt from the product slurry a) using a filtering basket centrifuge that has an internal slurry feed, a centrifuge basket, and an integral screen, the screen being used with or without at least one of an optional filter cloth or other porous barrier, which screen and optional filter cloth or other porous barrier retains solid material but allows liquid to pass through, said screen being disposed on an outer surface of the centrifuge basket and b) disposing a layer of coarse salt particles having an average particle size within a range of from 100 micrometers to 2000 micrometers on an inner surface of the centrifuge, said coarse salt particles lying atop an inner surface of the screen, or when at least one of the optional filter cloth or other porous barrier is used in conjunction with the screen, atop an inner surface of said optional filter cloth and/or other porous barrier, the coarse salt particles having an average particle size that exceeds that of the precipitated alkali metal salt or alkaline earth metal salt particles contained in the product slurry, whereby the precipitated alkali metal salt or precipitated alkaline earth metal salt forms a layer on a slurry feed side of the layer of coarse salt particles.

2. The method of claim 1, wherein the layer of coarse salt particles has a thickness within a range of from 10 millimeters to 150 millimeters.

3. The method of claim 1, further comprising a step of removing at least a portion of the precipitated alkali metal halide salt or alkaline earth metal halide salt layer.

4. The method of claim 3, wherein the step of removing at least a portion of the precipitated salt layer also removes at least an outer surface portion of the layer of coarse salt particles.

5. The method of claim 4, wherein the step of removing at least a surface portion of the layer of coarse salt particles results in a reduction of coarse salt layer thickness of at least 0.1 millimeter.

6. The method of claim 3, wherein the step of removing at least a portion of the precipitated salt layer has two sub-steps, sub-step a) which effects removal of substantially all of the precipitated salt layer from an outer surface of said layer of coarse salt particles and sequential sub-step b) which effects removal of at least the surface portion of the layer of coarse salt particles, said surface portion containing plugging amounts of organic contaminants that reduce rates of liquid filtration through the layer of coarse salt particles.

7. The method of claim 1, wherein separating the precipitated alkali metal halide salt or alkaline earth metal salt from the product slurry occurs as a batch process that comprises at least one sequential series of substeps, said substeps being a) filling a receiving portion of a centrifuge with an amount of the product slurry, the amount being less than that which overfills the receiving portion of the centrifuge, b) allowing a portion of liquids contained in the reaction mixture to drain through the layer of coarse salt particles, and c) operating the centrifuge at a speed sufficient to substantially effect separation of the amount of the reaction product mixture into a resin mixture component that substantially passes through the layer of coarse salt particles and the layer of precipitated alkali metal halide salt or alkaline earth metal halide salt.

8. The method of claim 1, wherein the particles of the coarse salt layer have a gross chemical composition substantially identical to that of salt particles contained in the product slurry.

9. A method for preparing a filter basket centrifuge for use in the improved method for producing an epoxy resin of claim 1, which method for preparing the centrifuge comprises establishing a layer of coarse salt particles, which layer has a slurry feed side and a filtrate side and disposing said layer such that the slurry feed side of the layer first contacts product slurry from a source of said product slurry and the filtrate side is spaced apart from said product slurry source.

10. The method of claim 9, which method comprises sub-steps a) introducing an aliquot of the coarse salt particles into the centrifuge, and b) forming the aliquot into a layer with a substantially uniform thickness.

* * * * *